United States Patent [19]

Strong

[11] Patent Number: 5,177,266
[45] Date of Patent: Jan. 5, 1993

[54] PROCCESS FOR THE MANUFACTURE OF 2-ALKOXYMETHYLACROLEIN

[75] Inventor: Henry L. Strong, Somerset, N.J.

[73] Assignee: American Cyanamid Company, Stamford, Conn.

[21] Appl. No.: 812,518

[22] Filed: Dec. 20, 1991

[51] Int. Cl.$^5$ .................. C07C 45/61; C07C 47/26
[52] U.S. Cl. ..................... 568/460; 568/420; 568/449; 568/459; 568/485; 568/496
[58] Field of Search ............. 568/449, 460, 496, 497, 568/687, 465, 463, 461, 420, 459, 485

[56] References Cited

U.S. PATENT DOCUMENTS

| 3,809,722 | 5/1974 | Bouniot | 568/465 |
| 4,552,985 | 11/1985 | Merger et al. | 568/465 |
| 4,723,011 | 2/1988 | Doehner, Jr. | 546/250 |
| 4,948,896 | 8/1990 | Nagao | 546/250 |
| 5,008,392 | 4/1991 | Meier et al. | 546/250 |

FOREIGN PATENT DOCUMENTS 0477994 12/1973 U.S.S.R. ............... 568/465

Primary Examiner—Werren B. Lone
Attorney, Agent, or Firm—Peggy A. Climenson

[57] ABSTRACT

There is provided a process for the manufacture of 2-alkoxymethylacrolein compounds via the reaction of an appropriate alcohol and acrolein in the presence of an acid and a trisubstituted amine to form an intermediate and the subsequent reaction of the intermediate with formaldehyde in the presence of an acid and a disubstituted amine.

20 Claims, No Drawings

PROCCESS FOR THE MANUFACTURE OF 2-ALKOXYMETHYLACROLEIN

BACKGROUND OF THE INVENTION

Although there are literature procedures which have been used successfully to prepare certain substituted acrolein compounds, there is, as yet, no known method reported for the manufacture of 2-alkoxy methylacrolein.

Alpha, beta-unsaturated aldehydes such as 2-alkoxymethylacrolein are useful in the preparation of substituted pyridine-2,3-dicarboxylates, which are key intermediates in the manufacture of a new class of imidazolinone herbicides. The use of $\alpha,\beta$-unsaturated aldehydes in the preparation of pyridine-2,3-dicarboxylates is described in U.S. Pat. Nos. 4,723,011, 4,948,896 and 5,008,392.

Therefore, it is an object of this invention to provide a convenient and effective method for the manufacture of 2-alkoxymethylacrolein compounds useful in the preparation of the herbicide intermediates.

SUMMARY OF THE INVENTION

The present invention relates to a process for the manufacture of compounds of formula I

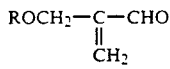

wherein R is $C_1$ to $C_6$ alkyl.

The formula I alkoxymethylacrolein compound is prepared by reacting an alcohol, ROH wherein R is as described for formula I, with at least one molar equivalent of acrolein in the presence of an acid, a catalytic amount of a trisubstituted amine and a solvent to form an intermediate and reacting said intermediate with at least one molar equivalent of formaldehyde in the presence of an acid, a catalytic amount of disubstituted amine and a solvent to obtain the desired formula I compound.

The invention further relates to a process for the manufacture of 2-alkoxymethylacrolein compounds of formula I which comprises reacting a suitable compound of formula II $$ROCH_2CH_2-W \qquad II$$

wherein R is as described for formula I and W is CHO or $CH(OR_1)_2$ and $R_1$ is $C_1$ to $C_4$ alkyl, with at least one molar equivalent of formaldehyde in the presence of an acid, a catalytic amount of a disubstituted amine and a solvent.

DESCRIPTION OF THE INVENTION

The present invention provides a process for the manufacture of compounds of formula I. The compounds of formula I may be used to prepare 5-(substituted)-pyridine-2,3-dicarboxylates which are key intermediate compounds in the preparation of 2-(imidazolin-2-yl)nicotinate herbicides. For example, the formula I compounds useful in the present invention may be reacted with an $\alpha$-halo-$\beta$-keto ester in the presence of an ammonium salt to form the corresponding pyridine-2,3-dicarboxylate product described in U.S. Pat. No. 4,723,011 and shown in flow diagram I.

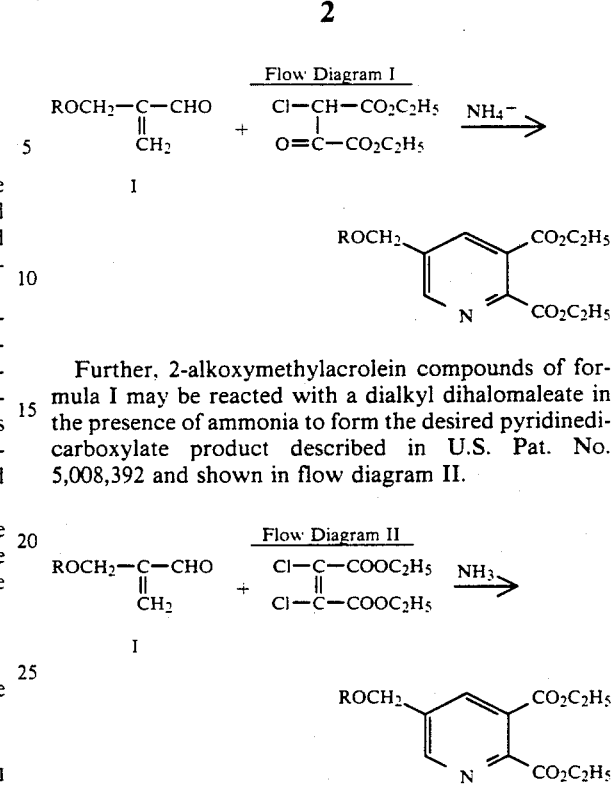

Further, 2-alkoxymethylacrolein compounds of formula I may be reacted with a dialkyl dihalomaleate in the presence of ammonia to form the desired pyridinedicarboxylate product described in U.S. Pat. No. 5,008,392 and shown in flow diagram II.

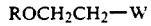

The thus-obtained pyridinedicarboxylate compounds may be converted to the corresponding herbicidal 2-(imidazolin-2-yl)nicotinic acids, esters and salts described in U.S. Pat. No. 4,798,619 and co-pending application Ser. No. 397,699, filed on Aug. 23, 1989.

Compounds of formula I are difficult to prepare using the Mannich-type conditions set forth in *Synthesis*, pp. 703-775 (1973). It has now been found, that the alkoxymethyl compounds of formula I may be effectively prepared in an efficient process from readily available starting materials. In accordance with the method of invention, an appropriate alcohol having the formula, ROH wherein R is $C_1$ to $C_6$ alkyl, may be reacted with at least one moler equivalent of acrolein in the presence of an acid, a catalytic amount of a trisubstituted amine and a solvent to form an intermediate and the intermediate may be reacted with at least one molar equivalent of formaldehyde in the presence of an acid, a disubstituted amine and a solvent to form the desired formula I alkoxymethylacrolein compound. The reaction is shown in flow diagram III.

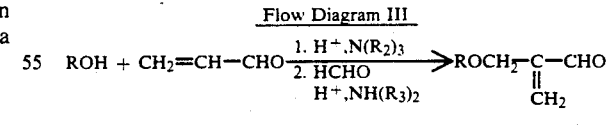

In general, the formation of the intermediate and the formula I product are temperature dependent, that is, increased reaction temperature increases the rate of formation. Convenient reaction times may be obtained by increasing the reaction temperature to about 20° to 110° C., preferably about 75° to 100° C. Suitable reaction solvents are water or mixtures of water and a water-miscible organic solvent. Acids suitable for use in the present process are strong mineral acids, preferably polybasic acids such as sulfuric acid and phosphoric acid. Trisubstituted amines, $N(R_2)_3$, wherein $R_2$ is $C_1-C_4$alkyl, $C_1-C_4$alkanol and the like are suitable for use in the present invention. Disubstitued amines, $NH(R_3)_2$, wherein $R_3$ is $C_1-C_6$alkyl, preferably dibutylamine, may be used in the inventive process. It is intended formaldehyde be used in any of its readily available forms and preferably as an aqueous solution of about 37% concentration.

Advantageously, compounds of formula I may also be prepared by reacting a compound of formula II $$ROCH_2CH_2-W \qquad \qquad II$$

wherein R is $C_1-C_6$alkyl and W is CHO or $CH(OR_1)_2$ and $R_1$ is $C_1-C_4$alkyl, with at least one molar equivalent of formaldehyde in the presence of an acid, a catalytic amount of a disubstituted amine, $NH(R_3)_2$ wherein $R_3$ is $C_1-C_4$alkyl, and a solvent. The reaction is shown in flow diagram IV.

Flow Diagram IV

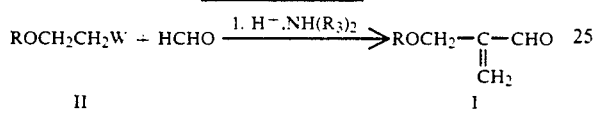

Compounds of formula II may be prepared according to methods known in the art such as that described by R. Hall and E. S. Stern, *Journal of the Chemical Society* (London), pp. 3388-3393 (1954). The formaldehyde employed in the above process may be in any of its readily available forms and preferably as an aqueous solution of about 37%. Acids suitable for use are strong mineral acids such as those mentioned hereinabove and preferably sulfuric acid or phosphoric acid. The reaction is temperature dependent, therefore convenient reaction times may be obtained by elevating the reaction temperature to about 20° to 110° C., preferably about 75° to 100° C.

In order to present a more clear understanding of the invention, the following examples are set forth. The examples are primarily for the purpose of demonstrating more specific details thereof and the invention is not to be limited thereby except as defined in the claims.

Unless otherwise noted, all parts are parts by weight. The term NMR designates nuclear magnetic resonance spectroscopy.

EXAMPLE 1

Preparation of 2-methoxymethylacrolein from acrolein

A stirred mixture of acrolein (112 g, 2.0 mole), methanol (310 g, 9.08 mole), triethanolamine (7.5 g, 0.05 mole) and 85% phosphoric acid (5.7 g, 0.049 mole) in water is heated at reflux temperature for 9 hours, cooled to room temperature and filtered. The filtrate is diluted with water and treated with a 37% formaldehyde solution (162 g, 2.0 mole formaldehyde), concentrated sulfuric acid (11.6 g, 0.11 mole), and dibutylamine (27 g, 0.21 mole), heated at reflux temperature for 4 hours, cooled to room temperature and extracted with methylene chloride. The extracts are combined and concentrated and the concentrate is vacuum distilled to give the title product, 88 g (44% yield) bp 64°-66°/70 mm Hg, identified by NMR analysis.

EXAMPLE 2

Preparation of 2-ethoxymethylacrolein from acrolein

A stirred mixture of anhydrous ethanol (235.5 g, 5.12 mole) and acrolein (77.3 g, 1.38 mole) is treated with 0.7 ml concentrated HCl and $NH_4Cl$ (6.0 g, 0.11 mole) and heated to reflux temperature over a 3 hour period. The reaction mixture is heated at reflux temperatures for 18 hours in a flask fitted with a 1 Dean Stark trap. The trap is removed and the reaction mixture is vacuum distilled. The distillate is redistilled, and 42 g is added to a stirred mixture of water, 0.8 g of concentrated $H_2SO_4$, hydroquinone (0.05 g, 0.45 mmole) and dibutylamine (1.78 g, 0.014 mole). A 37% formaldehyde solution (19.5 g, 0.24 mole) is added to the reaction mixture simultaneously at 80°-85° C. The reaction mixture is stirred for 6 hours at 80°-85° C., cooled to room temperature and extracted with hexanes. The extracts are combined and fractionally distilled to yield the title product, identified by NMR analysis.

EXAMPLE 3

Preparation of 2-methoxymethylacrolein from 1,1,3-trimethoxypropane

To a mixture of 96% sulfuric acid (3.0 g, 0.024 mole), dibutylamine (6.7 g, 0.052 mole) and hydroquinone (1.6 g, 0.013 mole) in water at 85° C., is added a mixture of 1,1,3-trimethoxypropane (120.6 g, 0.90 mole) and 37% formaldehyde solution (84 g, 1.1 mole formaldehyde) over a 1.25 hour period. The reaction mixture is heated at reflux temperature for 5 hours, cooled to room temperature and extracted with methylene chloride. The extracts are combined and fractionally distilled to give the title product, identified by NMR analysis.

EXAMPLE 4

Preparation of 2-methoxymethylacrolein from β-methoxymethylpropionaldehyde

A mixture of β-methoxymethylpropionaldehyde (44 g, 0.43 mole), 37% formaldehyde (40.5 g, 0.52 mole), dibutylamine (6.8 g, 0.053 mole), 96% sulfuric acid (3.0 g, 0.029 mole) and hydroquinone (0.6 g, 0.055 mole) in water is heated at reflux temperature for 2 hours, cooled to room temperature and extracted with methylene chloride. The extracts are combined and fractionally distilled to give the title product, 20.5 g (48% yield), identified by NMR analysis.

EXAMPLE 5

Preparation of 2-alkoxymethylacrolein from β-alkoxymethylpropionaldehyde

Using essentially the same procedure described in Example 4 and substituting the appropriate β-alkoxymethylpropionaldehyde, the following compounds are obtained: 2-butoxymethylacrolein, 1.4 g (28% yield), identified by NMR analysis and 2-isopropoxymethylacrolein, 1.4 g (22% yield), identified by NMR analysis.

I claim:

1. A process for the manufacture of a compound of formula I

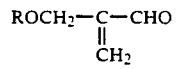

wherein R is $C_1$ to $C_6$ alkyl, which comprises reacting ROH wherein R is $C_1$ to $C_6$ alkyl with at least one molar equivalent of acrolein in the presence of a mineral acid, a catalytic amount of trisubstituted amine of the formula $N(R_2)_3$, wherein $R_2$ is $C_1$ to $C_4$ alkyl or $C_1$ to $C_4$ alkanol, a solvent, wherein the solvent is water or a mixture of water and a water-miscible organic solvent, to form an intermediate and reacting said intermediate with at least one molar equivalent of formaldehyde in the presence of a mineral acid, a catalytic amount of a disubstituted amine of the formula $NH(R_3)_2$, wherein $R_3$ is $C_1$ to $C_6$ alkyl, and a solvent, wherein the solvent is water or a mixture of water and a water-miscible organic solvent, to form the formula I compound.

2. The process according to claim 1, wherein the reaction is carried out at an elevated temperature.

3. The process according to claim 2, wherein the reaction temperature is about 20° C. to 110° C.

4. The process according to claim 1, wherein the acid is selected from the group consisting of sulfuric acid, phosphoric acid, hydrochloric acid and hydrobromic acid.

5. The process according to claim 4, wherein the acid is sulfuric acid or phosphoric acid.

6. The process according to claim 1, wherein the trisubstituted amine is selected from the group consisting of tri($C_1$-$C_4$alkyl)amine and tri($C_1$-$C_4$alkanol)amine.

7. The process according to claim 6, wherein the trisubstituted amine is triethylamine or triethanolamine.

8. The process according to claim 1, wherein the disubstituted amine is di($C_1$-$C_4$alkyl)amine.

9. The process according to claim 8, wherein the disubstituted amine is dibutylamine.

10. The process according to claim 1, wherein the solvent is water.

11. A process for the manufacture of compound of formula I

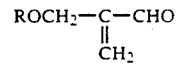

wherein R is $C_1$ to $C_6$ alkyl which comprises reacting a compound of formula II

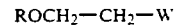

wherein R is $C_1$ to $C_6$ alkyl and W is CHO or $CH(OR_1)_2$ and $R_1$ is $C_1$ to $C_4$ alkyl, with at least one molar equivalent of formaldehyde in the presence of a mineral acid, a catalytic amount of a disubstituted amine of the formula $NH(R_3)_2$, wherein $R_3$ is $C_1$ to $C_6$ alkyl, and a solvent, wherein the solvent is water or a mixture of water and a water-miscible organic solvent.

12. The process according to claim 11, wherein W is CHO.

13. The process according to claim 11, wherein W is $CH(OR_1)_2$.

14. The process according to claim 11, wherein the reaction is run at an elevated temperature.

15. The process according to claim 14, wherein the reaction temperature is about 20° C. to 110° C.

16. The process according to claim 11, wherein the acid is selected from the group consisting of sulfuric acid, phosphoric acid, hydrochloric acid and hydrobromic acid.

17. The process according to claim 16, wherein the acid is sulfuric acid or phosphoric acid.

18. The process according to claim 11, wherein the disubstituted amine is di-($C_1$-$C_4$alkyl)amine.

19. The process according to claim 18, wherein the disubstituted amine is dibutylamine.

20. The process according to claim 11, wherein the solvent is water.